United States Patent [19]

Merrifield et al.

[11] Patent Number: 5,244,598

[45] Date of Patent: Sep. 14, 1993

[54] METHOD OF PREPARING AMINE FUNCTIONAL SILICONE MICROEMULSIONS

[75] Inventors: James H. Merrifield, Ballston Spa; Raymond J. Thimineur, Scotia; Frank J. Traver, Troy, all of N.Y.

[73] Assignee: General Electric Company, Waterford, N.Y.

[21] Appl. No.: 759,275

[22] Filed: Sep. 13, 1991

[51] Int. Cl.$^5$ .................. A61K 7/075; B01J 13/00; C09K 3/00

[52] U.S. Cl. .................. 252/314; 106/287.11; 252/312; 424/47; 424/70; 424/DIG. 1

[58] Field of Search .................. 252/312, 314; 106/287.11; 424/70

[56] References Cited

U.S. PATENT DOCUMENTS

| | | | |
|---|---|---|---|
| 3,544,498 | 12/1970 | Holdstock et al. | 524/588 |
| 3,748,275 | 7/1973 | Bernheim et al. | 252/312 |
| 4,559,227 | 12/1985 | Chandra et al. | 424/70 |
| 4,595,512 | 6/1986 | Tellier et al. | 252/312 X |
| 4,620,878 | 11/1986 | Gee | 106/287.15 |
| 4,631,273 | 12/1986 | Blehm et al. | 252/312 X |
| 4,785,067 | 11/1988 | Brumbill | 528/26 |
| 4,797,272 | 1/1989 | Linn et al. | 424/59 |
| 4,842,766 | 6/1989 | Blehm et al. | 252/309 |
| 5,064,694 | 11/1991 | Gee | 252/312 X |
| 5,077,040 | 12/1991 | Bergmann et al. | 424/70 |

Primary Examiner—Richard D. Lovering

[57] ABSTRACT

A method is provided for preparing an amino-functional polyorganosiloxane microemulsion having an average particle size of from about 0.015 to about 0.05 microns by (A) forming an oil mixture by blending (1) an amino-functional polyorganosiloxane and (2) at least one surfactant, wherein at least one of the surfactants is insoluble in the amino-functional polyorganosiloxane; (B) dropwise adding an initial portion of water to the oil and surfactant mixture prepared in step (A), agitating the mixture formed in step (B) for a period of time sufficient to form a homogeneous mixture; (C) adding water to the homogeneous mixture formed in (B); and (D) adding a lower aliphatic carboxylic acid having from 1 to about 4 carbon atoms or a mineral acid selected from HCl, $H_2SO_4$, $HNO_3$, HBr, or HI to the mixture formed in (C) in an amount sufficient to provide the mixture with a pH of from about 4 to about 7, the acid reacting with the amino-functional polyorganosiloxane (A)(1) to form a water-soluble salt. Also provided herein are the amino-functional polyorganosiloxane microemulsion formed by the method of the invention and hair care compositions containing the amino-functional polyorganosiloxane microemulsion.

19 Claims, No Drawings

METHOD OF PREPARING AMINE FUNCTIONAL SILICONE MICROEMULSIONS

BACKGROUND OF THE INVENTION

The present invention is related to a method for making microemulsions. More particularly, the present invention is related to a method for making microemulsions having an average particle size of 0.05 microns and below.

Microemulsions containing aminofunctional silicone fluids have been found to be useful in hair car compositions, such as hair conditioners. As defined herein, the term "microemulsions" refers to transparent, stable systems consisting of small droplets having an average diameter of 0.05 microns or below. The small size of the droplets makes the microemulsion transparent in appearance. Products containing microemulsions are valued for their stability and small particle size which gives the product increased aesthetic value.

The use of microemulsions in cosmetic compositions is known in the art. Reference is made, for example, to U.S. Pat. Nos. 4,797,272 (Linn et al.) and 4,620,878 (Gee).

U.S. Pat. No. 4,797,272 (Linn et al.) discloses water-in-oil microemulsion compositions having an average droplet size in the range of about 0.001 microns to about 0.2 microns in diameter and containing moisturizers or sunscreens, surfactants, oils (such as cyclic dimethyl polysiloxane compounds), and skin humectants.

U.S. Pat. No. 4,620,878 (Gee) discloses a polyorganosiloxane emulsion containing a polyorganosiloxane containing at least one polar radical, e.g., an amine radical, attached to Si through Si—Ci or Si—O—C bonds or at least one silanol radical and a surfactant which is insoluble in the polyorganosiloxane. The emulsion prepared in Gee has an average particle size of less than 0.14 microns and can be prepared by forming a translucent oil concentrate by mixing the polyorganosiloxane (which can be amino-functional), at least one surfactant, and water, and then forming a polyorganosiloxane emulsion of the oil-in-water type by rapidly dispersing the translucent oil concentrate in water.

It is continually desirable to provide alternative methods for preparing microemulsions of small average particle size.

The present invention is based on the discovery that the average particle size of an amino-functional silicone microemulsion can be reduced to a value in the range of from 0.015 to about 0.05 microns by adding a saturated, lower aliphatic carboxylic acid after the addition of water and surfactant to the amino-functional silicone fluid and further by adding the water in two separate portions wherein the first portion is added slowly to the silicone fluid and surfactant mixture.

SUMMARY OF THE INVENTION

In one aspect, the present provides a method of preparing a transparent amino-functional polyorganosiloxane microemulsion having an average particle size of from about 0.015 to about 0.050 microns, comprising the step of:

(A) forming an oil and surfactant mixture by blending:
  (1) 100 parts of an amino-functional polyorganosiloxane having an amino content of from about 0.6 to about 3.0 milliequivalents per gram and comprising:
    (a) $R_aQ_bSiO_{(4-a-b)/2}$ units; and
    (b) $R_cSiO_{(4-c)/2}$ units;
    wherein the molar ratio of $R_aQ_bSiO_{(4-a-b)/2}$ units to $R_cSiO_{(4-c)/2}$ units ranges from about 1:2 to about 1:64, "a" is a number in the range of 0-2, "b" is a number in the range of "1-3, "a"+"b" is less than or equal to 3, "c" is a number in the range of 1-3, R is a monovalent hydrocarbon or substituted hydrocarbon radical having from 1 to about 6 carbon atoms, and q is a polar radical having the general formula —$R^1NHZ$, wherein $R^1$ is a divalent linking group comprised of carbon and hydrogen atoms; carbon, hydrogen, and oxygen atoms; or carbon, hydrogen, and sulfur atoms; and Z is a radical selected from the group consisting of hydrogen atoms, alkyl radicals containing from 1 to 4 carbon atoms, and —$CH_2CH_2NH_2$ radicals; and
  (2) from about 10 to about 60 parts by weight per 100 parts of (A)(1) of at least one surfactant, wherein at least one of the surfactants is insoluble in the amino-functional polyorganosiloxane;

(B) dropwise adding water to the oil and surfactant mixture prepared in step (A), the water being added for a period of from about 5 to about 60 minutes in an amount ranging from about 5 to about 40 parts by weight based on the weight of the oil and surfactant mixture, the mixture containing the oil and surfactant mixture and the water added thereto being agitated during the addition of the water such that a homogeneous mixture is formed of the water and the oil and surfactant mixture;

(C) adding water to the homogeneous mixture formed in (B), the water being added in an amount such that the total amount of water added in (B) and (C) is in the range of from about 500 to about 1000 parts by weight based on the weight of the mixture formed in (A); and (D) adding a lower aliphatic saturated carboxylic acid having from 1 to about 4 carbon atoms or a mineral acid selected from HCl, $H_2SO_4$, $HNO_3$, HBr, or HI to the mixture formed in (C) in an amount sufficient to provide the mixture with a pH of from about 4 to about 7, the acid reacting with the amino-functional polyorganosiloxane (A)(1) to form a water-soluble salt.

Other aspects of the present invention are the amino-functional polyorganosiloxane microemulsions formed by the method of the invention and hair care compositions containing the amino-functional polyorganosiloxane microemulsions.

DETAILED DESCRIPTION OF THE INVENTION

Amino-functional polyorganosiloxane microemulsions prepared by the method of this invention have an average particle size of from about 0.015 to about 0.05, preferably from about 0.015 to about 0.04, and most preferably from about 0.015 to about 0.025, microns.

In step (A) of the method of this invention, an oil and surfactant mixture is prepared by blending (1) 100 parts of an amino-functional polyorganosiloxane and (2) from about 10 to about 60 parts by weight of at least one surfactant, wherein at least one of the surfactants is insoluble in the amino-functional polyorganosiloxane.

The amino-functional polyorganosiloxane of (A)(1) has an amino content of from about 0.6 to about 3.0, preferably from about 0.6 to about 1.5, and most preferably from about 0.6 to about 1.0 milliequivalents per gram, and comprises:

(a) $R_aQ_bSiO_{(4-a-b)/2}$ units; and
(b) $R_cSiO_{4-c)/2}$ units.

In the formula above, R is a monovalent hydrocarbon or substituted hydrocarbon radical having from 1 to about 6 carbon atoms. Q is a polar radical having the general formula $R^1NHZ$, wherein $R^1$ is a divalent linking group comprised of carbon and hydrogen atoms; carbon, hydrogen, and oxygen atoms; or carbon, hydrogen, and sulfur atoms. Z is a radical selected from the group consisting of hydrogen atoms, alkyl radicals containing from 1 to 4 carbon atoms, and —$CH_2CH_2NH_2$ radicals.

Examples or radicals represented by R include alkyl radicals such as methyl, ethyl, propyl, butyl, amyl, and hexyl; alkenyl radicals such as vinyl and allylradicals; cycloalkyl radicals such as cyclobutyl and cyclohexyl radicals; and phenyl radicals; the corresponding halohydrocarbon radicals such as 3-chloropropyl, 4-bromobutyl, 3,3,3-trifluoropropyl, chlorocyclohexyl, bromophenyl, and chlorophenyl radicals; and the corresponding mercaptohydrocarbon radicals such as mercaptoethyl, mercaptopropyl, mercaptohexyl, and mercaptophenyl.

Preferably, R is an alkyl radical containing from 1 to 4 carbon atoms and most preferably R is methyl.

Examples of $R^1$ include methylene, ethylene, propylene, hexamethylene, decamethylene, —$CH_2CH(CH_3(CH_2—$, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)$-$C(O)OCH_2$—, —$(CH_2)_3C(O)OCH_2CH_2$—, —$C_6H_4C_6$-$H_4$—, —$C_6H_4CH_2C_6H_4$, and —$(CH_2)_3C(O)SCH_2C$-$H_2$—.

Preferably, $R^1$ is a divalent hydrocarbon radical containing from 2 to about 10 carbon atoms and most preferably from 3 to 4 carbon atoms.

Z is most preferably a —$CH_2CH_2NH_2$ radical.

Therefore, Q is most preferably an amine-functional polar radical having the formula —$CH_2CH_2CH_2NHCH_2CH_2NH_2$.

In the formulas for the units (a) and (b) of (A)(1), "a" is a number in the range of 0–2, "b" is a number in the range of 1–3, "a"+"b" is less than or equal to 3, and "c" is a number in the range of 1–3.

The molar ratio of $R_aQ_bSiO_{(4-a-b)/2}$ units to $R_cSiO_{(4-c)/2}$ units ranges from about 1:2 to about 1:65, preferably from about 1:5 to about 1:65, and most preferably from about 1:15 to about 1:20.

The most preferred aminofunctional silicone fluids (A)(1) for use in this invention has the formula

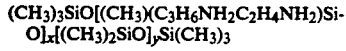

wherein x is an umber in the range of from 1 to about 20 and preferably about 8, and y is a number in the range of from about 20 to about 800 and preferably about 275.

(A)(2) contains at least one surfactant, wherein at least one of the surfactants is insoluble in the aminofunctional silicone of (A)(1). The surfactant which is insoluble in the amino-functional silicone of (A)(1) will be referred to herein as the "primary surfactant" while the other surfactants will be referred to as "secondary surfactants."

The surfactant or blend of surfactants has a hydrophilic-lipophilic balance value of from about 10 to about 16, preferably from about 12 to about 16, and most preferably from about 13 to about 14.

The primary surfactant may be cationic, nonionic, or amphoteric in nature. Examples of such surfactants are known in the art and are disclosed, for example, in U.S. Pat. No. 4,620,878 to Gee, which is hereby incorporated by reference herein. Generally, nonionic surfactants are preferred for use in this invention.

Surfactants useful as the primary surfactant in the present invention include the sorbitan esters of fatty acids having 10 to 22 carbon atoms; polyoxyethylene sorbitan esters of $C_{10}$ to $C_{22}$ fatty acids having up to 95% ethylene oxide; polyoxyethylene sorbitol esters of $C_{10}$ to $C_{22}$ fatty acids, polyoxyethylene derivatives of fatty phenols having 6 to 20 carbon atoms and up to 95% ethylene oxide; fatty amino and amido betaines having 10 to 22 carbon atoms; and polyethylene condensates of $C_{10}$ to $C_{22}$ fatty acids or fatty alcohols having up to 95% ethylene oxides.

Surfactants preferred for use as the primary surfactant in this invention include the octylphenoxy polyethoxy ethanols, which are nonionic surfactants with varying amounts of ethylene oxide units available from Union Carbide Corporation under the general Triton tradename; trimethylnonyl polyethylene glycol ethers and polyethylene glycol ethers of linear 11–15 carbon atoms containing alcohols, available from Union Carbide Corporation under the general tradename Tergitol; the nonionic ethoxylated tridecyl ethers, available from Emery Industries under the general tradename Trycol, polyethoxylated quaternary ammonium salts and ethylene oxide condensation products of the fatty amines available from Armak Company under the general tradenames Ethoquad and Ethomeen, respectively, and alkoxylated siloxane surfactants containing ethylene oxide and/or propylene oxide groups. These preferred surfactants may also be obtained from other suppliers under different tradenames.

The preferred surfactant for use as the primary surfactant in this invention are the trimethylnonyl polyethylene glycol ethers and polyethylene glycol ethers of linear 11–15 carbon atoms containing alcohols, available from Union Carbide Corporation under the general tradename Tergitol. The most preferred surfactant for use as the primary surfactant is a trimethyl nonyl polyethylene glycol ether.

The secondary surfactants may be anionic, cationic, nonionic or amphoteric and may be either soluble or insoluble in the aminofunctional silicone of (A)(1). Nonionic surfactants are preferred as the secondary surfactant in this invention. Examples of surfactants which are soluble in the aminofunctional silicone include the alkyl phenol ethoxylates.

Preferably, the secondary surfactant used in this invention is also insoluble in the aminofunctional silicone of (A)(1). The preferred surfactant for use as the secondary surfactant in this invention is a 70% aqueous solution of octylphenoxy polyethoxy (40) ethanol.

Preferably, (A)(2) is a mixture of two nonionic surfactants, preferably of trimethyl nonyl polyethylene glycol ether (primary surfactant) and 705 aqueous solution of octylphenoxy polyethoxy (40) ethanol (secondary surfactant), at a primary surfactant:secondary surfactant weight ratio of from about 1:2 to about 5:1, preferably from about 1:1 to about 3:1, and most preferably from about 1.8:1 to about 2.2:1.

The amount of (A)(2) is in the range of from about 10 to about 60, preferably from about 20 to about 40, and most preferably from about 25 to about 35, parts by weight per 100 parts of (A)(1).

After the oil and surfactant mixture of (A) has been formed, water is added dropwise to the oil and surfactant mixture in an amount ranging from about 5 to about 40 parts by weight per 100 parts of (A) for a period of from about 5 to about 60 minutes.

The amount of water added in step (B) is preferably from about 15 to about 50, and most preferably from about 15 to about 25 parts by weight per 100 parts of (A).

The mixture formed in step (B) is agitated for a period of time sufficient to form a homogeneous mixture, typically about 5 to about 50 minutes. The mixture containing the oil and surfactant mixture and the water added thereto in step (B) is agitated during the addition of the water such that a homogeneous mixture is formed of the water and the oil and surfactant mixture, typically about 5 to about 60 minutes. The length of time needed to form a homogeneous mixture in step (B) will depend on the mixing equipment parameters and can be determined by those skilled in the art without the undue experimentation.

In step (C), water is added to the homogeneous mixture formed in step (B). The water in step (C) is added in an amount such that the total amount of water added in steps (B) and (C) is in the range of at least 50 parts by weight and preferably from about 100 to about 2000 parts by weight, and most preferably from about 300 to about 500 parts by weight, per 100 parts of the mixture formed in step (A).

It is critical to the present invention that water be added in two separate steps, i.e., steps (B) and (C), because if water is not added in that manner, a translucent to opaque macroemulsion will result.

In step (D), a lower aliphatic carboxylic acid having from 1 to about 4 carbon atoms or a mineral acid selected from HCl, $H_2SO_4$, $HNO_3$, HBr, and HI is added to the mixture formed in step (C).

The lower carboxylic acid which can be used in step (D) of the method of this invention has from 1 to about 4 carbon atoms, preferably from about 2 to about 4, carbon atoms, and most preferably 2 carbon atoms, i.e., acetic acid.

It is critical to the present invention that the number of carbon atoms in the carboxylic acid not exceed 4 carbon atoms because if it does, a translucent to opaque macroemulsion will result.

The acid in step (D) may also be a mineral acid selected from HCl, $H_2SO_4$, $HNO_3$, HBr, and HI. Of these, HCl is preferred.

The most preferred acid for use in step (C) is acetic acid.

The acid in step (D) is added in an amount sufficient to provide the mixture with a pH of from about 4 to about 7, preferably from about 4.5 to about 6 and most preferably about 4.5. The amount of acid needed to provide such pH values will depend on the amount of the amino-functional silicone fluid (A)(1) and the amino content of the amino-functional silicone fluid. With an amino-functional silicone fluid having an amino content of 0.6 milliequivalents per gram, the amount of acid sufficient to provide a pH with the desired range will be about 2.5 parts by weight per 100 parts of the amino-functional silicone fluid. With an amino-functional silicone fluid having an amino content of 3 milliequivalents per gram, the amount of acid will be about 12.5 parts by weight per 100 parts of the fluid. With an amino-functional silicone fluid having an amino content in the preferred range of 0.6 to 1.5 milliequivalents per gram, the amount of acid will vary from 1.0 to about 6 parts per 100 parts of the amino-functional silicone fluid and with an amino-functional silicone fluid having an amino content in the preferred range of 0.6 to 1.0 milliequivalents per grams, the amount of acid will vary from 1.0 to about 4 parts of the amino-functional silicone fluid.

It is critical to the present invention that the acid be added after the addition of water and surfactant to the amino-functional silicone fluid, i.e., after steps (A)–(C) have been taken. If added prior to that time, a translucent to opaque macroemulsion or gel will result.

Preferably, the method of this invention further comprises the step (E) of adding an effective amount of glycerol, a water-soluble alkylene glycol or a water-soluble polyalkylene glycol to the mixture formed in step (D). Component (E) functions to improve the clarity of the emulsion and is added in an amount effective to achieve that. The amount of component (E) typically ranges in the amount of from about 2 to about 20, preferably from about 2 to about 12, and most preferably from about 4 to about 8, parts by weight based on the weight of the mixture formed in step (D).

Examples of suitable water-soluble alkylene glycols for use in step (E) include ethylene glycol and propylene glycol. Examples of suitable water-soluble polyalkylene glycols include the polyethylene glycols of the carbowax variety, available from Union Carbide Corporation.

Glycerol is the most preferred ingredient added in step (E).

Preferably, the method of this invention further comprises the step (F) of adding an effective amount of a biocide to the mixture formed in step (E) in order to protect the composition against the growth of potentially harmful microorganisms. Examples of biocides useful herein include alkyl esters of para-hydroxybenzoic acid, hydantoin derivatives, propionate salts, and a variety of quaternary ammonium compounds. Examples of specific biocides include methyl and propyl para-hydroxybenzoates, imidazolidinyl urea, quaternium-15, and Dowicil 200 which is cis-1-(3-chloroally)-3,5,7-triazo-1-azo-niaadamantane chloride.

The amount of biocide added in step (F) will depend on the type of biocide used. Dowicil 200 is typically added at about 2 to about 5 parts by weight based on the weight of the mixture formed in step (A).

In another aspect, the present invention is directed to the amino-functional silicone fluid prepared according to the method described above.

The present invention is further directed to a personal care composition comprising by weight:

(l) 100 parts of the amino-functional polyorganosiloxane prepared according to the method of this invention; and (ll) an effective amount of a cosmetically acceptable carrier medium.

For the cosmetically acceptable carrier medium (ll), the term "cosmetically acceptable" is intended to mean that it is suitable for contact with the human body and, more specifically, in contact with human hair. Aqueous carrier mediums are frequently used. Specific carrier mediums will vary according to the type of personal care product in which the composition of this invention will be used.

Examples of personal care products which may contain the compositions of this invention include lipsticks, eye-shadows, bronzes, blushes, lotions, handcreams, antiperspirants, shampoos, hair conditions, emolients, antiseptics, sunscreen agents, cleansing agents, hair styling products, hair sprays, spritzes, and other skin care and hair care products.

Another type of carrier medium which can be used in this invention is a composition dispensed from an aerosol container in the form of a collapsible foam aerosol hair product referred to as a "mousse" product. Such "mousse" products are described, for example, in U.S. Pat. No. 4,536,390 to Padden, which is hereby incorporated by reference herein.

Another type of carrier medium which can be used in this invention is a cosmetically acceptable solvent such as ethanol, isopropanol, volatile polydimethylsiloxane and polydimethylcyclosiloxane fluids.

If a self-pressurized aerosol spray is desired, then conventional propellants such as volatile hydrocarbons such as n-propane, isopropane, n-butane and isobutane can be used as well as compressed gases such as nitrogen and carbon dioxide.

Other carrier media will be apparent to those of ordinary skill in the art.

The carrier medium (II) is used in an effective amount which will depend on the particular application in which it is used. Typically, the amount of the carrier medium will vary from about 300 to about 10,000 parts by weight per 100 parts of (I).

Most preferably, the amino-functional silicone fluids prepared according to the method of this invention are used in hair care compositions.

In order that those skilled in the art will be better able to practice the present invention, the following examples are given by way of illustration and not by way of limitation. All parts and percentages are by weight, unless otherwise noted.

EXPERIMENTAL

In the examples below, the following terms have the meanings below:

"Microemulsion"—refers to the microemulsion prepared in Example 1.
"Microemulsion"—refers to the microemulsion prepared in Example 2.
"Amino-functional silicon fluid"—a high viscosity amino functional-dimethyl silicone polymer having an amino content of about 0.75 to about 0.85 milliequivalent per gram and having the formula $(CH_3)_3SiO[(CH_3)(CH_2CH_2CH_2NHCH_2CH_2NH_2)SiO]_x[(CH_3)_2SiO]_ySi)CH_3)_3$ wherein x is 8 and y is 275.
"Pentamer"—decamethylcyclopentasiloxane.

EXAMPLE 1

Example 1 illustrates the method of this invention for preparing microemulsions of amino-functional silicone fluids.

The aminofunctional silicone fluid (about 200 grams) was blended with a nonionic surfactant mixture containing 10 grams of a trimethyl nonyl polyethylene glycol ether (know as Tergitol TMN-6) and 5 grams of a 70% aqueous octylphenoxy polyethoxy (40) ethanol (known as Triton X-405). An initial portion of water (3.4 grams) was then slowly added to the mixture. The mixture was stirred for about 15 minutes to insure homogeneity. The remainder of the water was then added, this latter portion of the water being added more rapidly than the initial portion above. The emulsion had a particle size of about 70 nm and has a bluish-white, opaque appearance. About 0.2% by weight of acetic acid was added to the emulsion. The resulting emulsion was translucent and had a particle size of about 0.025 microns and a solids content of about 25%. Glycerol (0.5% by weight) was added to the emulsion to increase clarity. Dowicil ®200 (0.2% by weight), a biocide, was then added to the emulsion.

EXAMPLE 2

Example 2 illustrates the preparation of an amino-functional silicone macroemulsion used in the comparative examples below.

To a clean, stainless steel beaker were added 350 grams of the amino-functional silicone fluid, 40 grams of Tertitol TMN-6, and 20 grams of Triton X-405. The mixture was blended and heated to 40° C. Sixty grams of water were slowly added with agitation to the mixture. The mixture was invented using a colloid mill. The resulting paste was diluted in approximately 400 grams of water to form an emulsion. After the emulsion was stirred for 10 minutes, its solids content was adjusted to 35% by adding water. The resulting emulsion was opaque and had an average particle size of about 0.2 to about 0.6 microns.

COMPARATIVE EXAMPLES A-C AND EXAMPLES 3-5

Six hair conditioning compositions were prepared, having the formulations shown in Table 1 below.

The compositions in Examples 3-5 contained the microemulsion prepared in Example 1. The compression in Comparison Examples A and B contained the macroemulsion prepared in Example 2. The composition in Comparison Example C did not contain either a macroemulsion to a microemulsion.

TABLE 1

Examples 3-5 & Comparison Example A-C; Formulation Formulations (parts by weight)

| Ingredient | Ex. A | Ex. B | Ex. C | Ex. 3 | Ex. 4 | Ex. 5 |
|---|---|---|---|---|---|---|
| Varisoft ® CRC | 5.00 | 5.00 | 5.00 | 5.00 | 5.00 | 5.00 |
| Citric Acid | 0.05 | 0.05 | 0.05 | 0.05 | 0.05 | 0.05 |
| Dowacil 200 | 0.10 | 0.10 | 0.10 | 0.10 | 0.10 | 0.10 |
| Macro-emulsion | 0 | 3.00 | 3.00 | 0 | 0 | 0 |
| Micro-emulsion | 0 | 0 | 0 | 5.00 | 5.00 | 3.00 |
| Pentamer | 0 | 0 | 1.50 | 0 | 1.50 | 0 |
| Water | 94.85 | 91.85 | 90.35 | 89.85 | 88.35 | 91.85 |
| Total | 100.0 | 100.0 | 100.0 | 100.0 | 100.0 | 100.0 |

The compositions prepared in Comparative Examples A-C and Examples 3-5 were each applied to a separate tress of freshly washed, wet, dark brown, virgin hair and rinsed. Wet and dry combining properties were evaluated as the tresses were dried. Shine, static, and softness properties were also evaluated. The following scale was used to evaluate the properties measured in these examples:

1=very poor, no effect
2=poor, barely perceptible effect
3=fair, perceptible but less than acceptable effect 4=acceptable, generally typical or average effect
5=good, slightly better than average effect
6=very good, distinctively visible effect
7=excellent, highly visible and highly discernable effect The evaluations of the properties of the compositions prepared in Comparative Examples A-C and Examples 3-5 are shown in Table 2 below.

TABLE 2

Examples 3-5 & Comparison Example A-C; Property Evaluations

| Example No. | Wet/Dry Combing | All Properties |
|---|---|---|
| A | 5.0 | 4.8 |
| B | 4.8 | 4.7 |
| C | 4.8 | 5.0 |
| 3 | 6.0 | 6.2 |
| 4 | 6.3 | 6.4 |
| 5 | 5.7 | 5.7 |

The results shown in Table 2 illustrate that the microemulsion of this invention provides significantly better overall performance than the macroemulsion or no emulsion at all.

What is claimed is:

1. A method of preparing a transparent amino-functional polyorganosiloxane microemulsion having an average particle size of from about 0.015 to about 0.050 microns, comprising the steps of:
   (A) forming an oil and surfactant mixture by blending:
      (1) 100 parts of an amino-functional polyorganosiloxane having an amino content of from about 0.6 to about 3.0 milliequivalents per gram and comprising:
         (a) $R_aQ_bSiO_{(4-a-b)/2}$ units; and
         (b) $R_cSiO_{(4-c)/2}$ units;
      wherein the molar ratio of $R_aQ_bSiO_{(4-a-b)/2}$ units to $R_cSiO_{4-c)/2}$ units ranges from about 1.2 to about 1:65, "a" is a number in the range of 0-2, "b" is a number in the range of 1-3, "a"+"b" is less than or equal to 3, "c" is a number in the range of 1-3, R is a monovalent hydrocarbon or substituted hydrocarbon radical having from 1 to about 6 carbon atoms, and q is a polar radical having the general formula —$R^1NHZ$, wherein $R^1$ is a divalent linking group comprised of carbon and hydrogen atoms; carbon, hydrogen, and oxygen atoms; or carbon, hydrogen, and sulfur atoms; and Z is a radical selected from the group consisting of hydrogen atoms, alkyl radicals containing from 1 to 4 carbon atoms, and —$CH_2CH_2NH_2$ radicals; and
      (2) from about 10 to about 60 parts by weight per 100 parts of (A)(1) of at least one surfactants, wherein at least one of the surfactants is insoluble in the amino-functional polyorganosiloxane;
   (B) dropwise adding water to the oil and surfactant mixture prepared in step (A), the water being added for a period of from about 5 to about 60 minutes in an amount ranging from about 5 to about 40 parts by weight based on the weight of the oil surfactant mixture, the mixture containing the oil and surfactant mixture and the water added thereto being agitated during the addition of the water such that a homogeneous mixture is formed of the water and the oil and surfactant mixture;
   (C) adding water to the homogeneous mixture formed in (B), the water being added in an amount such that the total amount of water added in (B) and (C) is in range of from about 500 to about 1000 parts by weight based on the weight of the mixture formed in (A); and
   (D) adding an acid selected from the group consisting of a lower aliphatic saturated carboxylic acid having from 1 to about 4 carbon atoms, HCl, $H_2SO_4$, $HNO_3$, HBr and HI to the mixture formed in (C) in an amount sufficient to provide the mixture with a pH of from about 4 to about 7, the acid reacting with the amino-functional polyorganosiloxane (A)(1) to form a water-soluble salt.

2. A method according to claim 1 wherein the microemulsion has an average particle size of from about 0.015 to about 0.04 microns.

3. A method according to claim 2 wherein the microemulsion has an average particle size of from about 0.015 to about 0.025 microns.

4. A method according to claim 1 wherein the amino-functional silicone fluid has an amino content of from about 0.6 to about 1.5 milliequivalents per gram, R is an alkyl radical having from 1 to about 4 carbon atoms, $R^1$ is a divalent hydrocarbon radical containing from 2 to about 10 carbon atoms, Z is a —$CH_2CH_2NH_2$ radical, and the molar ratio of $R_aQ_bSiO_{4-a-b)/2}$ units to $R_cSiO_{4-c)/2}$ units ranges from about 1:5 to about 1:65.

5. A method according to claim 4 wherein the amino-functional silicone fluid has an amino content of from about 0.6 to about 1.0 milliequivalent per gram, R is methyl, $R^1$ is a divalent hydrocarbon radical containing from 3 to 4 carbon atoms, and the molar ratio of $R_aQ_bSiO_{4-1-b)/2}$ units to $R_cSiO_{4-c)/2}$ units ranges from about 1:5 to about 1:20.

6. A method according to claim 5 wherein the amino-functional silicone fluid has the formula

$(CH_3)_3SiO[(CH_3)(C_3H_6NH_2C_2H_4NH_2)SiO]_x[(CH_3)_2SiO]_ySi(CH_3)_3$ wherein x is a number in the range of from 1 to about 20 and y is a number in the range of from about 20 to about 800.

7. A method according to claim 6 wherein x is about 8 and y is about 275.

8. A method according to claim 1 wherein (A)(2) is present in an amount within the range of from about 20 to about 40 parts by weight per 100 parts of (A)(1).

9. A method according to claim 8 wherein (A)(2) is present in an amount within the range of from about 25 to about 35 parts by weight per 100 parts by (A)(1).

10. A method according to claim 1 wherein the insoluble surfactant is a non-ionic surfactant having a hydrophilic-lipophilic balance value of from about 10 to about 16 and is selected from the group consisting of octylphenoxy polyethoxy ethanols, trimethylnonyl polyethylene glycol ethers, polyethylene glycol ethers of 11-15 carbon atoms containing alcohols, polyethoxylated quaternary salts, ethylene oxide condensation products of primary fatty amines, alkoxylated siloxanes containing ethylene oxide units, and alkoxylated siloxanes containing ethylene oxide and propylene oxide units.

11. A method according to claim 1 wherein (A)(2) is a nonionic surfactant mixture containing trimethyl nonyl polyethylene glycol ether and a 70% aqueous solution of octylphenoxy polyethoxy (40) ethanol at a weight ratio of trimethyl nonyl polyethylene glycol ether: 70% aqueous solution of octylphenoxy polyethoxy (40) ethanol of from about 1:2 to about 5:1.

12. A method according to claim 1 wherein the acid in step (D) is a lower aliphatic carboxylic acid having from 2 to about 4 carbon atoms.

13. A method according to claim 12 wherein the carboxylic acid is acetic acid.

14. A method according to claim 1 wherein the carboxylic acid in step (D) is used in an amount sufficient to provide a pH of from about 4.5 to about 6.

15. A method according to claim 14 wherein the carboxylic acid in step (d) is used in an amount sufficient to provide a pH of about 4.5.

16. A method according to claim 1 further comprising the step (E) of adding an amount of glycerol or polyalkylene glycol, effective to improve clarity of the emulsion, the parts by weight being based on the weight of the mixture formed in step (D).

17. A method according to claim 1 further comprising the step of adding an effective amount of a biocide.

18. A method according to claim 1 wherein the insoluble surfactant is a nonionic surfactant having a hydrophilic-lipophilic balance value of from about 10 to about 16 and is a polyethylene glycol ether of linear 11–15 carbon atoms containing alcohol.

19. A method according to claim 1 wherein the insoluble surfactant is a nonionic surfactant having a hydrophilic-lipophilic balance value of from about 10 to about 16 and is an ethoxylated tridecyl ether.

* * * * *